United States Patent [19]
Collard et al.

[11] Patent Number: 5,523,442
[45] Date of Patent: Jun. 4, 1996

[54] SILYLATED ACETYLCHOLINESTERASE INHIBITORS

[75] Inventors: Jean-Noël Collard, Illkirch; Jean-Marie Hornsperger, Griesheim-près-Molsheim, both of France

[73] Assignee: Merrell Pharmaceuticals Inc., Cincinnati, Ohio

[21] Appl. No.: 491,965

[22] PCT Filed: Jan. 25, 1994

[86] PCT No.: PCT/US94/00720

§ 371 Date: Jul. 18, 1995

§ 102(e) Date: Jul. 18, 1995

[87] PCT Pub. No.: WO94/19356

PCT Pub. Date: Sep. 1, 1994

[30] Foreign Application Priority Data

Feb. 16, 1993 [EP] European Pat. Off. ............. 93400385

[51] Int. Cl.$^6$ ................................. C07F 7/08; C07F 7/10
[52] U.S. Cl. .................. 556/413; 556/415; 556/418; 556/436; 556/437; 556/432; 556/431; 556/422; 556/428; 556/440; 556/449; 522/4
[58] Field of Search ........................ 556/413, 415, 556/418, 436, 437, 432, 431, 422, 428, 440, 449; 524/63; 552/4

[56] References Cited

U.S. PATENT DOCUMENTS

| | | |
|---|---|---|
| 3,651,115 | 3/1972 | Belsky et al. |
| 4,835,099 | 5/1989 | Mize et al. |
| 4,914,221 | 4/1990 | Winkler et al. |
| 5,008,425 | 4/1991 | Stahly . |
| 5,106,530 | 4/1992 | Haas et al. ............... 556/418 X |
| 5,171,750 | 12/1992 | Brossi et al. |
| 5,210,247 | 5/1993 | Haberle et al. ............... 556/413 |
| 5,389,619 | 2/1995 | Doetzer et al. ............... 514/63 |

FOREIGN PATENT DOCUMENTS 0403713 12/1990 European Pat. Off. .
0409676 1/1991 European Pat. Off. .

OTHER PUBLICATIONS

Gelb et al., Biochemistry, vol. 24, No. 8, pp. 1813–1817 (1985).
U. Brodbeck et al., Biochimica et Biophysica Acta, 567, pp. 357–369 (1979).
K. N. Allen et al., Biochemistry 28, pp. 8466–8473 (1989).
H. K. Nair, et al., J. Am. Chem. Soc., 115, pp. 9939–9941 (1993).
R. L. Metcalf et al., J. Econ. Entomol. 58, p. 1151 (1965).
A. Aberman et al., Biochimica et Biophysica Acta, 791; pp. 278–280 (1984).
R. L. Salvador et al., Tetrahedron. vol. 27, pp. 1221–1226 (1971).

*Primary Examiner*—Paul F. Shaver
*Attorney, Agent, or Firm*—Carolyn D. Moon

[57] ABSTRACT

Fluorinated silylated aromatic compounds, their intermediates, methods of use in treating diseases associated with deficiencies of cholinergic transmission in the central nervous system and methods for their preparation are disclosed.

17 Claims, No Drawings

SILYLATED ACETYLCHOLINESTERASE INHIBITORS

This application is a 371 of PCT/US96/0672 filed Jan. 25, 1994.

This invention relates to fluorinated silylated aromatic compounds, their intermediates, methods of use in treating diseases associated with deficiencies of cholinergic transmission in the central nervous system and methods for their preparation.

Compounds of the present invention have the following Formula I:

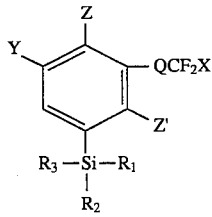

stereoisomers or mixtures thereof, or pharmaceutically acceptable salts thereof, wherein:

each of Z and Z' are independently H or F, provided that at least one of Z or Z' is F;

Q is

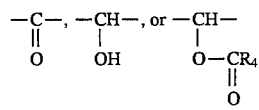

X is H, Br, Cl, F or $CF_3$;

Y is H, OH, $(C_{1-6})$ alkyl, $-(CH_2)_mOR_5$, hydroxy$(C_{1-6})$ alkyl, $(CH_2)_nNR_6R_6'$, azido, CN, $CO_2R_4$, $COR_6$, $SO_3H$, Br, Cl, F, $NO_2$ or $-(CH_2)_nSiR_1'R_2'R_3'$, provided that when both Z and Z' are F then Y is H or F;

$R_1$, $R_2$, $R_3$, $R_1'$, $R_2'$ and $R_3'$ are each independently $C_{1-10}$ alkyl or $(CH_2)_{n''}$ aryl;

$R_4$ is H, $(C_{1-10})$ alkyl, phenyl, benzyl or phenethyl;

$R_5$ is H, $(C_{1-10})$ alkyl, benzyl or phenethyl;

$R_6$ and $R_6'$ are independently hydrogen or $C_{1-10}$ alkyl;

m is an integer of 0, 1, 2, 3 or 4; and n, n' and n" are each independently an integer of 0, 1 or 2.

The compounds of the present invention are used to treat patients having conditions responsive to the acetylcholinesterase-inhibiting properties of the present compounds such as in the treatment of Degenerative Dementias.

The terms "$(C_{1-6})$ alkyl" and "$(C_{1-10})$ alkyl" mean straight or branched chain alkyl radicals containing respectively from 1 to 6 carbon atoms and from 1 to 10 carbon atoms, including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl, n-hexyl and so on. Likewise, the terms "$(CH_2)_n$" or "$(CH_2)_m$" may represent alkylene chains which may be branched or straight-chained.

"Hydroxy $(C_{1-6})$ alkyl" means a $(C_{1-6})$ alkyl group having from 1 to 3 hydroxy substituents thereon. Preferably, there is only one hydroxy substituent at the alpha position (attached to the carbon atom which is directly attached to the phenyl).

"Ts" or "tosyl" means

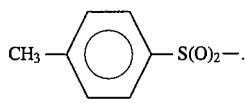

Tosyl derivatives mean

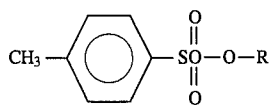

wherein R is $C_{1-6}$ alkylene.

"Aryl" includes both carbocyclic and heterocyclic moieties of which phenyl, pyridyl, indolyl, indazolyl, furyl and thienyl are of primary interest; these moieties being inclusive of their position isomers such as, for example, 2-, 3-, or 4-pyridyl, 2- or 3-furyl and thienyl, 1-, 2-, or 3-indolyl or the 1- and 3-indazolyl, as well as the dihydro and tetrahydro analogs of the furyl and thienyl moieties. Also included within the term "aryl" are such fused carbocyclic moieties as pentalenyl, indenyl, naphthalenyl, azulenyl, heptalenyl, acenaphthylenyl, fluorenyl, phenalenyl, phenanthrenyl, anthracenyl, acephenanthrylenyl, aceanthrylenyl, triphenylenyl, pyrenyl, chrysenyl, and naphthacenyl. Also included within the term "aryl" are such other heterocyclic radicals as 2- or 3-benzo[b]thienyl, 2- or 3-naphtho-[2,3-b]thienyl, 2- or 3-thianthrenyl, 2H-pyran-3-(or 4- or 5-)yl, 1-isobenzofuranyl, 2H-chromenyl-3-yl, 2- or 3-phenoxathiinyl, 2- or 3-pyrrolyl, 4- or 3-pyrazolyl, 2-pyrazinyl, 2-pyrimidinyl, 3-pyridazinyl, 2-indolizinyl, 1-isoindolyl, 4H-quinolizin-2-yl, 3-isoquinolyl, 2-quinolyl, 1-phthalazinyl, 1,8-naphthyridinyl, 2-quinoxalinyl, 2-quinazolinyl, 3-cinnolinyl, 2-pteridinyl, 4aH-carbazol-2-yl, 2-carbazolyl, β-carbolin-3-yl, 3-phenanthridinyl, 2-acridinyl, 2-perimidinyl, 1-phenazinyl, 3-isothiazolyl, 2-phenothiazinyl, 3-isoxazolyl, 2-phenoxazinyl, 3-isochromanyl, 7-chromanyl, 2-pyrrolin-3-yl, 2-imidazolidinyl, 2-imidazolin-4-yl, 2-pyrazolidinyl, 3-pyrazolin-3-yl, 2-piperidyl, 2-piperazinyl, 1-indolinyl, 1-isoindolinyl, 3-morpholinyl, benzo[h]isoquinolinyl, and benzo[b]furanyl, including the position isomers thereof except that the heterocyclic moieties cannot be attached directly through their nitrogen atoms. Aryl groups can be substituted or unsubstituted with one, two or three substituents independently selected from $C_{1-6}$ alkyl, haloalkyl, alkoxy, thioalkoxy, aminoalkylamino, dialkylamino, hydroxy, halo, mercapto, nitro, carboxaldehyde, carboxy, carboalkoxy and carboxamide.

$R_1$, $R_2$, $R_3$, $R_1'$, $R_2'$, and $R_3'$ are each independently selected from $C_{1-10}$ alkyl or $(CH_2)_{n''}$ aryl which means that, for example, $R_1$ could be benzyl while $R_2$ is methyl. In other words, none of $R_1$, $R_2$, $R_3$, $R_1'$, $R_2'$, or $R_3'$ have to be the same moiety, although this may be the case.

"Stereoisomers" for the compounds of Formula I is a general term for all isomers of individual molecules that differ only in the orientation of their atoms in space. It includes mirror image isomers (enantiomers), geometric isomers (cis/trans), and isomers of compounds with more than one chiral center that are not mirror images of one another (diastereoisomers), whichever forms are applicable to the compound.

The pharmaceutically acceptable salts of the compounds of Formula I include salts formed with non-toxic organic or inorganic acids such as, for example, from the following acids: hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic and benzenesulfonic.

The term "patient" refers to a warm-blooded animal, such as for example rats, mice, dogs, cats, guinea pigs, primates and humans. "Treating" a patient means to prevent or alleviate the patient's disease or condition.

The term "Degenerative Dementia" as used herein means senile dementia, presenile dementia, degenerative dementia of the Alzheimer's type (which includes Alzheimer's Disease) and other types of progressively deteriorating organic mental syndromes in which there is impairment in short-term and long-term memory. The Degenerative Dementia can be mild (impairment of work or social activities but able to live alone), moderate (some degree of supervision needed), or severe (continual supervision required).

Impairment in short-term memory is the inability to learn new information and may be demonstrated by, for example, the patient's inability to remember three objects after five minutes. Long-term memory impairment is the inability to remember information that was known in the past and may be indicated by, for example, the patients' inability to remember past personal information such as their birthplace, address, occupation, what happened yesterday, etc., or the inability to remember facts of common knowledge. There is typically impairment in abstract thinking, impairment in judgment, personality changes or other disturbances of higher cortical functions.

The preparation of the compounds of Formula I may be accomplished in a variety of methods depending upon the specific combinations of variable substituents. The following schemes illustrate only one way these compounds may be made. Other analogous chemical reactions and procedures may be utilized which may be known to those skilled in the art.

SCHEME A

To make the sub-generic Formula II:

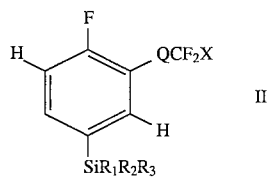

wherein
X = X' or CF$_3$;
X' = H, Br, Cl, or F; and R$_1$, R$_2$, R$_3$, and Q are as previously defined.

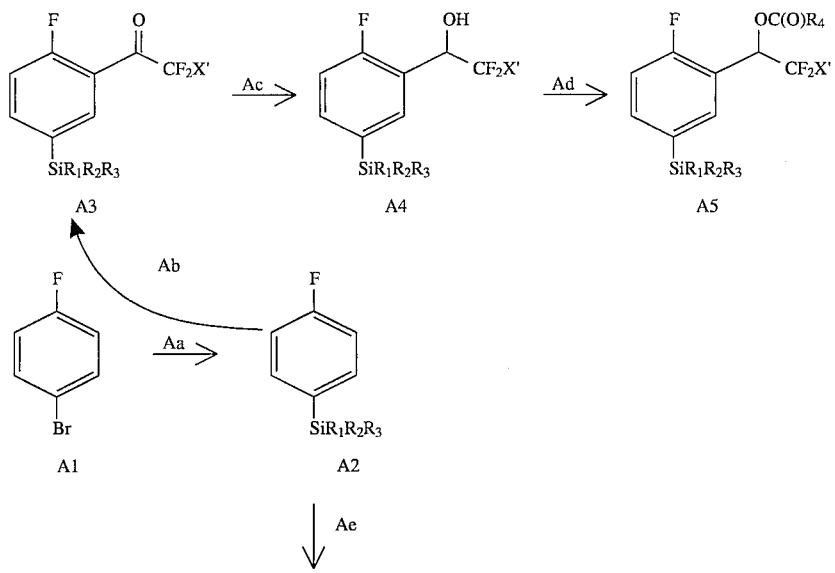

-continued
SCHEME A

[Structures A6, A7, A8, A9, A10 with transformations Af, Ag, Ac, Ad]

A6: 2-fluoro-5-($SiR_1R_2R_3$)benzoic acid

A7: Weinreb amide derivative (N-OCH$_3$, N-CH$_3$)

A8: aryl pentafluoroethyl ketone ($CF_2CF_3$)

A9: alcohol (OH, $CF_2CF_3$)

A10: ester (OC(O)$R_4$, $CF_2CF_3$)

All substituents are as previously defined unless otherwise stated. All starting materials are either commercially available or can be readily prepared by those skilled in the art.

Step Aa: $A_1 \rightarrow A_2$

The reaction involves the treatment of 4-bromo-1-fluoro benzene with $ClSiR_1R_2R_3$ in the presence of one equivalent of magnesium in a suitable solvent such as diethylether or tetrahydrofuran at the reflux temperature of the mixture. The silyl derivatives $ClSiR_1R_2R_3$ are obtained from tetrachlorosilane ($SiCl_4$) and successive alkylations with organomagnesium halide derivatives of the appropriate $R_1$, $R_2$ and $R_3$ substituents. For example, $SiCl_4$ is reacted with $R_1Mg$ halides to produce $R_1SiCl_3$ compounds which are reacted with $R_2Mg$ halides to produce $R_1R_2SiCl_2$ compounds which are reacted with $R_3Mg$ halides to produce $R_1R_2R_3SiCl$ compounds.

Step Ab: $A_2 \rightarrow A_3$

The 4-fluorotrialkylsilylphenyl compounds are converted to their lithium salts by reaction with an alkyllithium reagent at −50° C. in tetrahydrofuran and those intermediates to the desired products by reaction with two equivalents of the appropriate ester ($XCF_2CO_2R$, with R being preferably ethyl or methyl and X being any suitable halogen) or acid lithium salt ($XCF_2CO_2Li$) followed by hydrolysis with aqueous ammonium chloride.

Step Ac: $A_3 \rightarrow A_4$

The ketones are converted to alcohols preferably by using sodium tetraborohydride or sodium cyanoborohydride in ethanol, followed by hydrolysis with aqueous ammonium chloride.

Step Ad: $A_4 \rightarrow A_5$

The alcohols are esterfied preferably with an acyl chloride [($ClCOR_4$)] in the presence of triethylamine in a solvent such as dichloromethane.

Step Ae: $A_2 \rightarrow A_6$

Following Step Ab the lithium salt intermediates are reacted with carbon dioxide to produce carboxylic acids.

Step Af: $A_6 \rightarrow A_7$

Acids are reacted with isobutylchloroformate in the presence of triethylamine or N-methyl morpholine in tetrahydrofuran to form mixed anhydrides. Addition of molar equivalent amount of N,O-dimethylhydroxylamine to the anhydrides gives dimethylhydroxamic acid derivatives.

Step Ag: $A_7 \rightarrow A_8$

Dimethyl hydroxamic acid derivatives are converted to the pentafluoroketones preferably by treatment with a pentafluoroethyl anion generated insitu by contacting pentafluoroethyl iodide with a methyllithium-lithium bromide complex in an inert solvent, preferably diethyl ether. Hydrolysis is performed with aqueous ammonium chloride.

Reference is later made herein to a combination of steps of Scheme A as follows:

Sa=steps Ab+Ac+Ad

Sb=steps Ae+Af+Ag+Ac+Ad

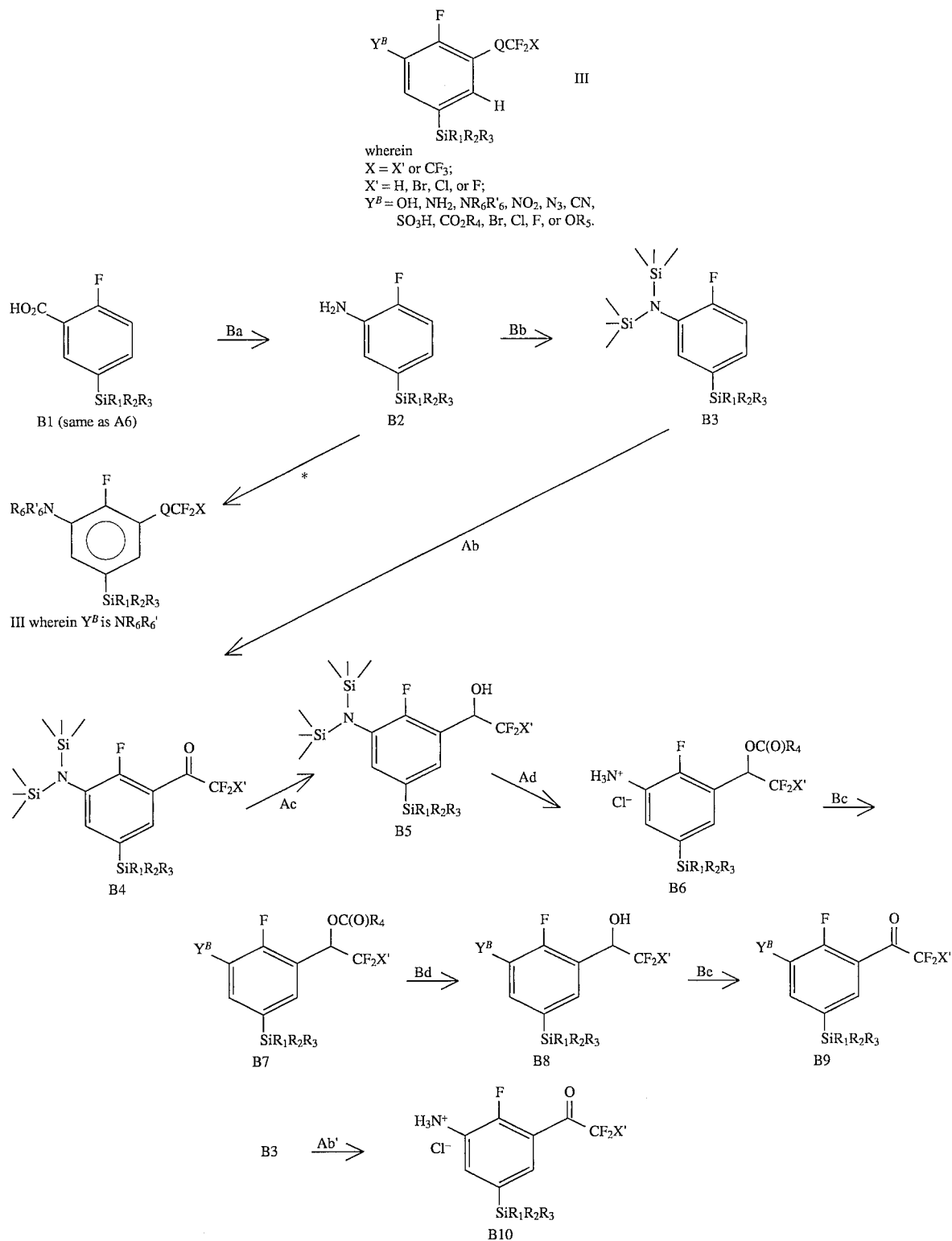

-continued
SCHEME B:
Preparation of compound having the subgeneric Formula III:
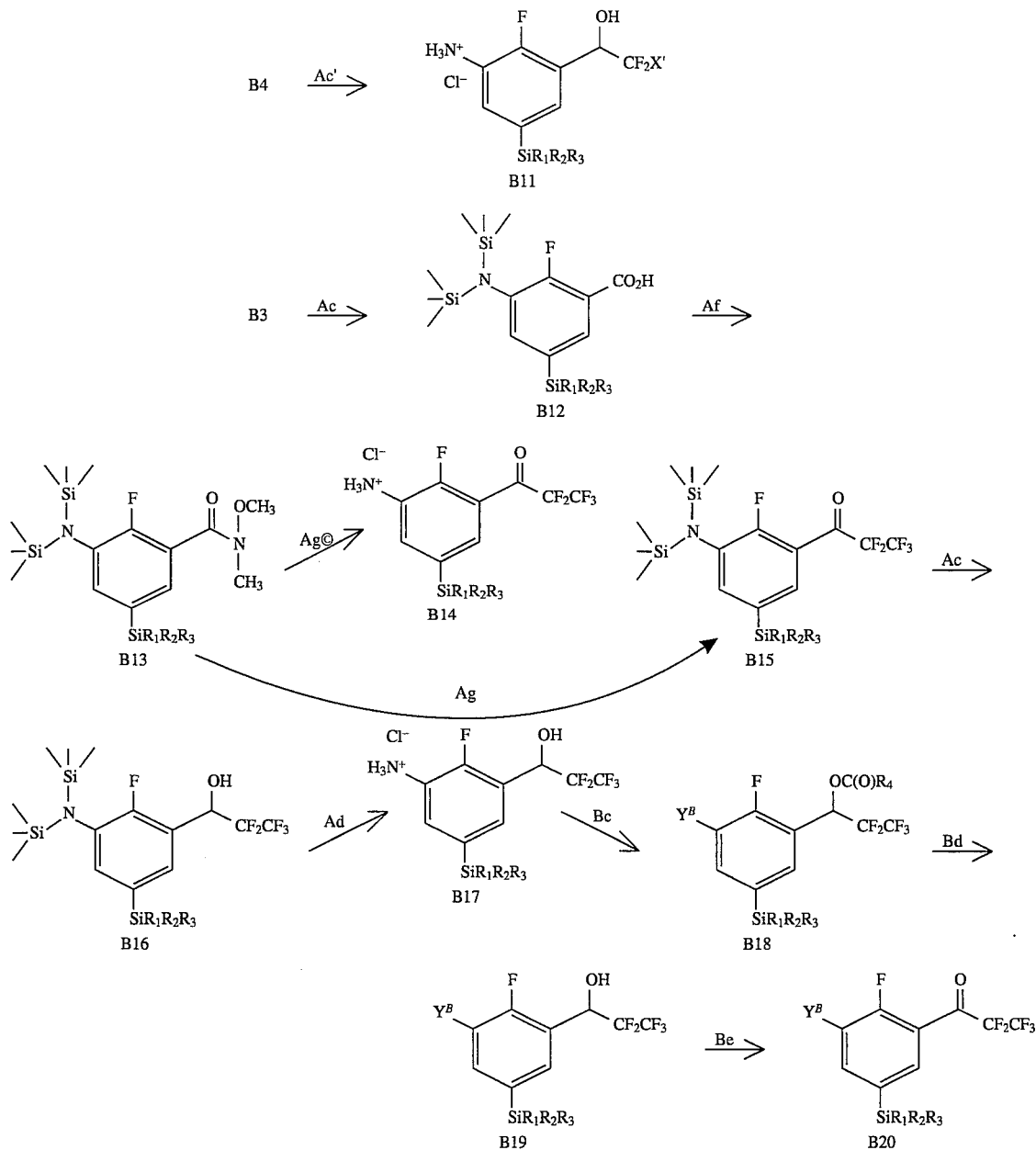

-continued
SCHEME B:
Preparation of compound having the subgeneric Formula III:

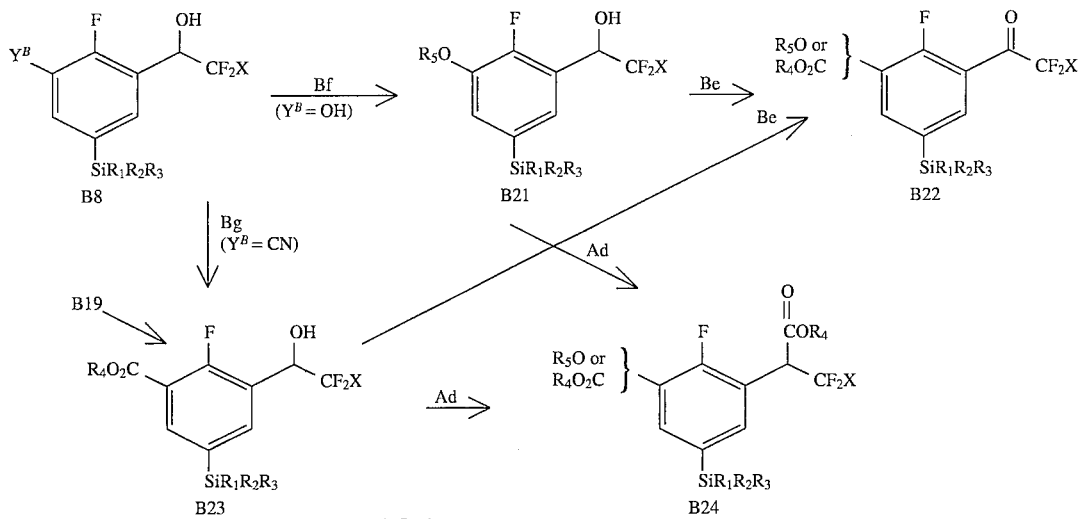

*See Scheme D: Df, Dg, Dh, Sa, b or Df, Dg, Di, Sa, b

Step Ba: $B_1(A_6) \rightarrow B_2$

Carboxylic acids $A_6$ are reacted with excess of thionyl chloride at reflux temperature to produce acyl chlorides which are reacted with sodium azide at 0° C. in acetone-water to produce acyl azides which are heated in benzene or toluene at reflux temperature and then treated with hydrochloric acid at reflux temperature to produce amine hydrochloride salts $B_2$.

Step Bb: $B_2 \rightarrow B_3$

Amine hydrochloride salts $B_2$ are converted to their free amines with aqueous sodium hydroxide and then treated with two equivalents of alkyllithium followed by two equivalents of chlorotrimethylsilane in diethyl ether or tetrahydrofuran at −60° C. to produce bistrimethylsilylated amines $B_3$.

Step Ab: $B_3 \rightarrow B_4 \rightarrow B_5$

Conversion of $B_3$ to $B_4$, then to $B_5$ by Steps Ab and Ac as previously described.

Step Ad': $B_5 \rightarrow B_6$

Following the procedure described in Step Ad the resulting esters are treated with a normal solution of hydrochloric acid.

Step Bc: $B_6 \rightarrow B_7$ and $B_{17} \rightarrow B_{18}$

When $Y^B$=Cl, CN, or $N_3$: The amine hydrochloride salts ($B_6$ and $B_{17}$) are treated with sodium nitrite in water to produce diazonium salts which are heated with cuprous chloride to produce chloroderivatives, or treated with cuprous cyanide to produce nitrile derivatives, or treated with sodium azide to produce azides.

When $Y^B$=Br: The amine hydrochloride salts ($B_6$ and $B_{17}$) are converted to their free amines with aqueous sodium bicarbonate. The free amines are dissolved in aqueous hydrobromic acid, treated with sodium nitrite and then with copper powder to produce bromide derivatives.

When $Y^B$=F or $NO_2$: The amine hydrochloride salts ($B_6$ and $B_{17}$) are converted to their free amines with aqueous sodium bicarbonate. The free amines dissolved in aqueous fluoroboric acid are treated with sodium nitrite. The diazonium fluoroborate salts are filtered and dried. They are then heated to produce fluoro derivatives or treated with sodium nitrite in the presence of copper powder to produce nitro derivatives.

When $Y^B$=OH: After conversion of the amine hydrochloride salts ($B_6$ and $B_{17}$) to their free amines, the amines are dissolved in aqueous sulfuric acid, diazoted with sodium nitrite and heated to produce phenol derivatives.

When $y^B$=$SO_3H$: After conversion of the amine hydrochloride salts to their free amines, the amines are dissolved in an aqueous mixture of sulfuric acid and phosphoric acid, diazoted with sodium nitrite and treated with sulfur dioxide. The reaction mixture is poured onto hydrated ferrous sulfate and copper powder to produce sulfinic acid.

Step Bd: $B_7 \rightarrow B_8$ and $B_{18} \rightarrow B_{19}$

Esters $B_7$ and $B_{18}$ are hydrolized with lithium hydroxyde in aqueous dimethoxyethane to produce alcohols $B_8$ and $B_{19}$.

Step Be: $B_8 \rightarrow B_9$ and $B_{19} \rightarrow B_{20}$

Alcohols $B_8$ and $B_{19}$ are oxidized with pyridinium dichromate or with Dess-Martin periodinane oxidant in dichloromethane or with the Swern Reaction to produce ketones $B_9$ and $B_{20}$.

Steps Ab', Ac' and Ag': respectively $B_3 \rightarrow B_{10}$; $B_4 \rightarrow B_{11}$; and $B_{13} \rightarrow B_{14}$ Procedure Ab, Ac or Ag is used as described previously, except hydrolysis is performed with a normal solution of hydrochloric acid.

Step Bf: $B_8$ or $B_{19} \rightarrow B_{21}$

Phenol derivatives $B_8$ or $B_{19}$ are converted to their sodium or potassium salt with sodium or potassium hydroxide, or sodium or potassium carbonate in water or acetone and reacted with alkyl bromide or iodide to produce $C_{1-6}$ alkoxy derivatives.

Step Bg: $B_8$ or $B_{19} \rightarrow B_{23}$

Nitrile derivatives are heated in aqueous hydrochloric acid to produce acids ($R_4$=H) or treated with an alcohol saturated with dry hydrochloric acid followed by hydrolysis with aqueous sodium bicarbonate to produce esters' ($R_4$ different from H).

SCHEME C: to make the subgeneric Formula IV:

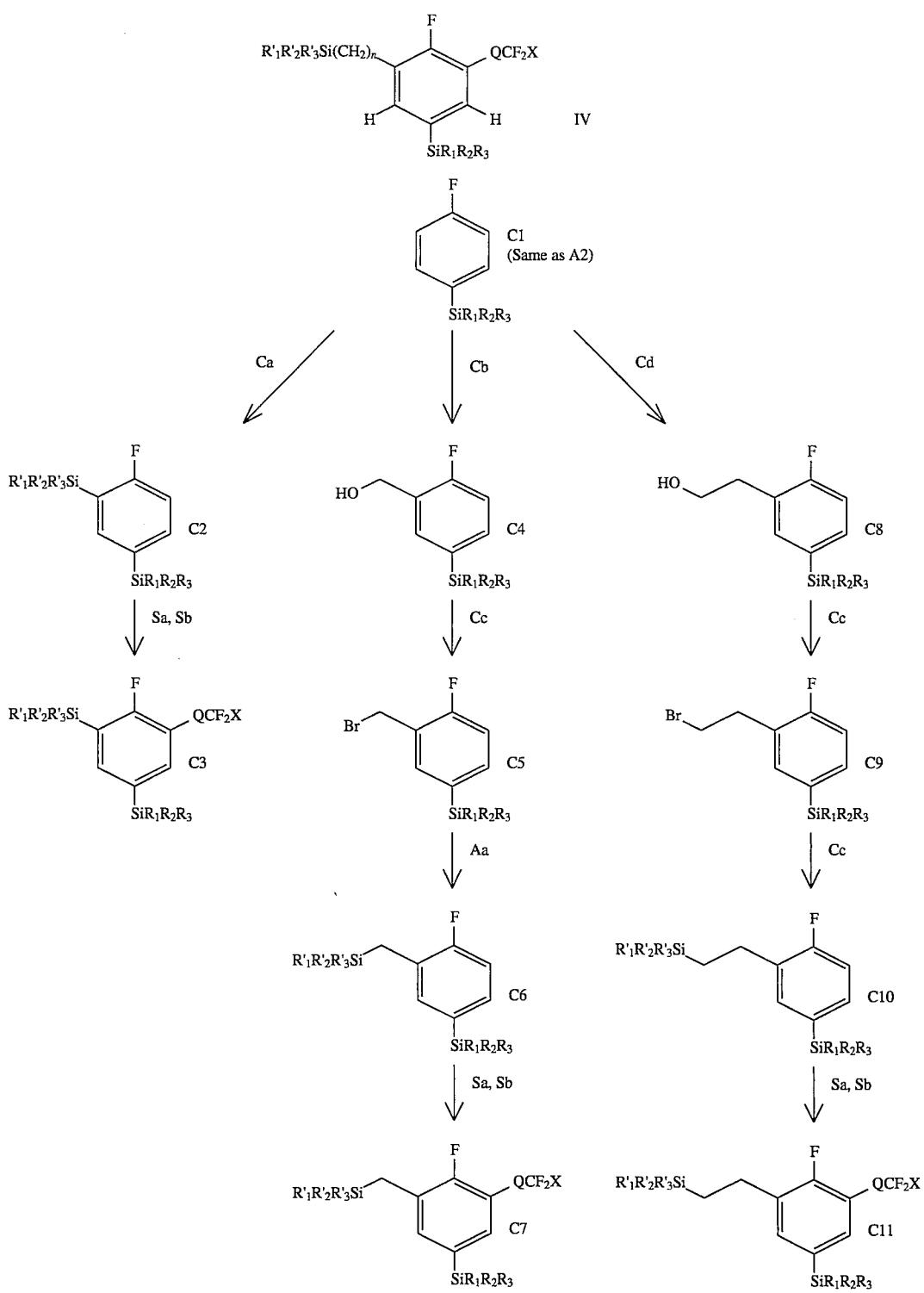

Step Ca: $C_1(A_2) \rightarrow C_2$:

Following the procedure described in Step Ab the lithium salts are treated with chlorotrisubstituted silane to produce bis-silylated derivatives $C_2$.

Step Cb: $C_1 \rightarrow C_4$:

Following the procedure described in Step Ab the lithium salts are treated with paraformaldehyde to produce benzyl alcohol derivatives $C_4$.

Step Cc: $C_4 \rightarrow C_5$:

Benzyl alcohols are heated with phosphorous tribromide to produce benzyl bromide derivatives $C_5$.

Step Cd: $C_1 \rightarrow C_8$:

Following the procedure described in Step Ab the lithium salts are treated with ethylene oxide to produce phenethyl alcohol derivatives $C_8$.

The remaining reactions indicate the steps previously described which are used.
SCHEME D:
to make the subgeneric Formula V:
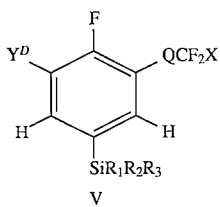
V
$Y^D$ = ($C_{1-6}$) alkyl, $COR_6$, hydroxy ($C_{1-6}$) alkyl, $(CH_2)_n NR_6 R_6'$, or $(CH_2)_m OR_5$.
Ts = Tosyl and derivatives thereof.
R = ($C_{1-6}$) alkyl or hydrogen.
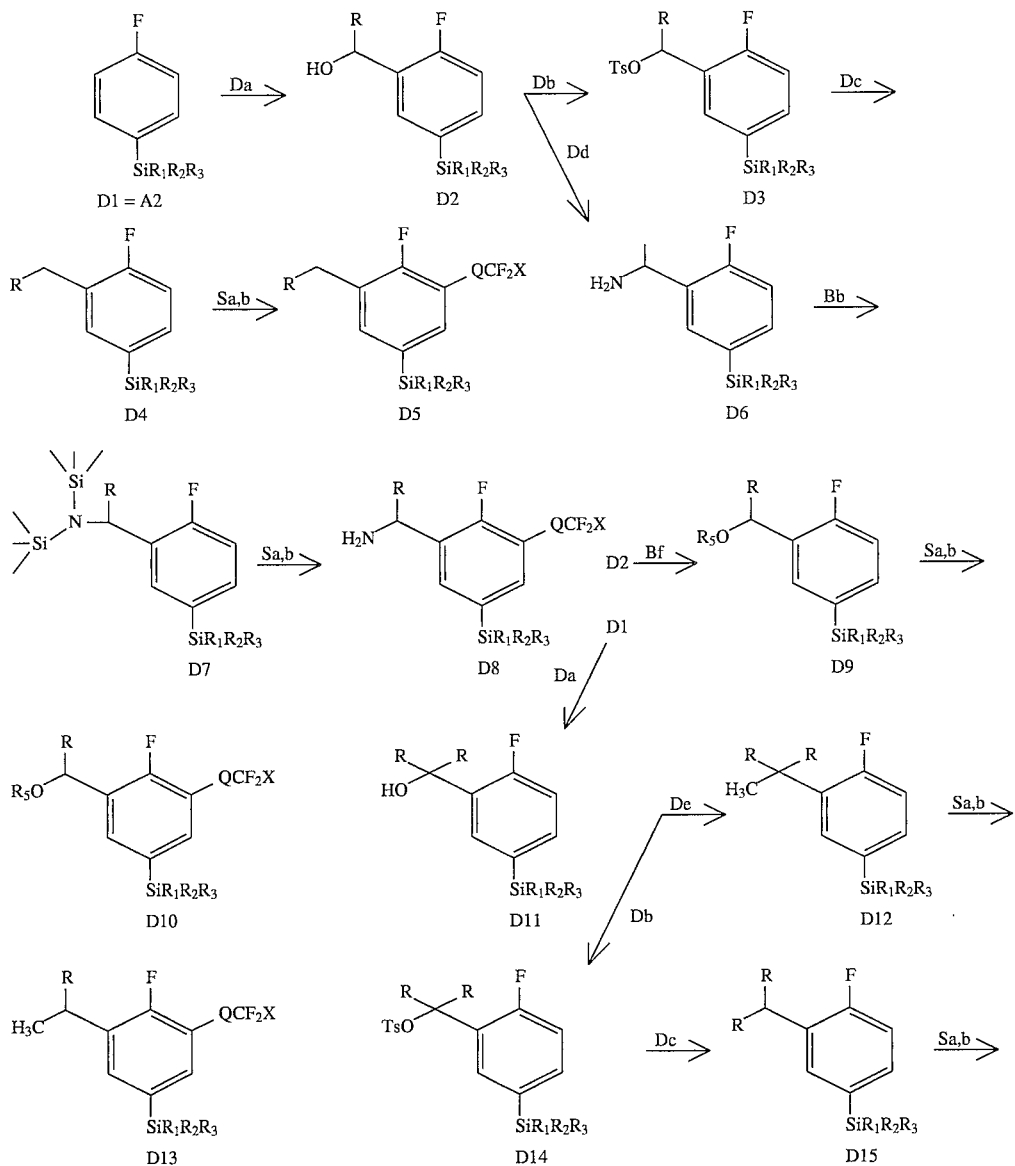

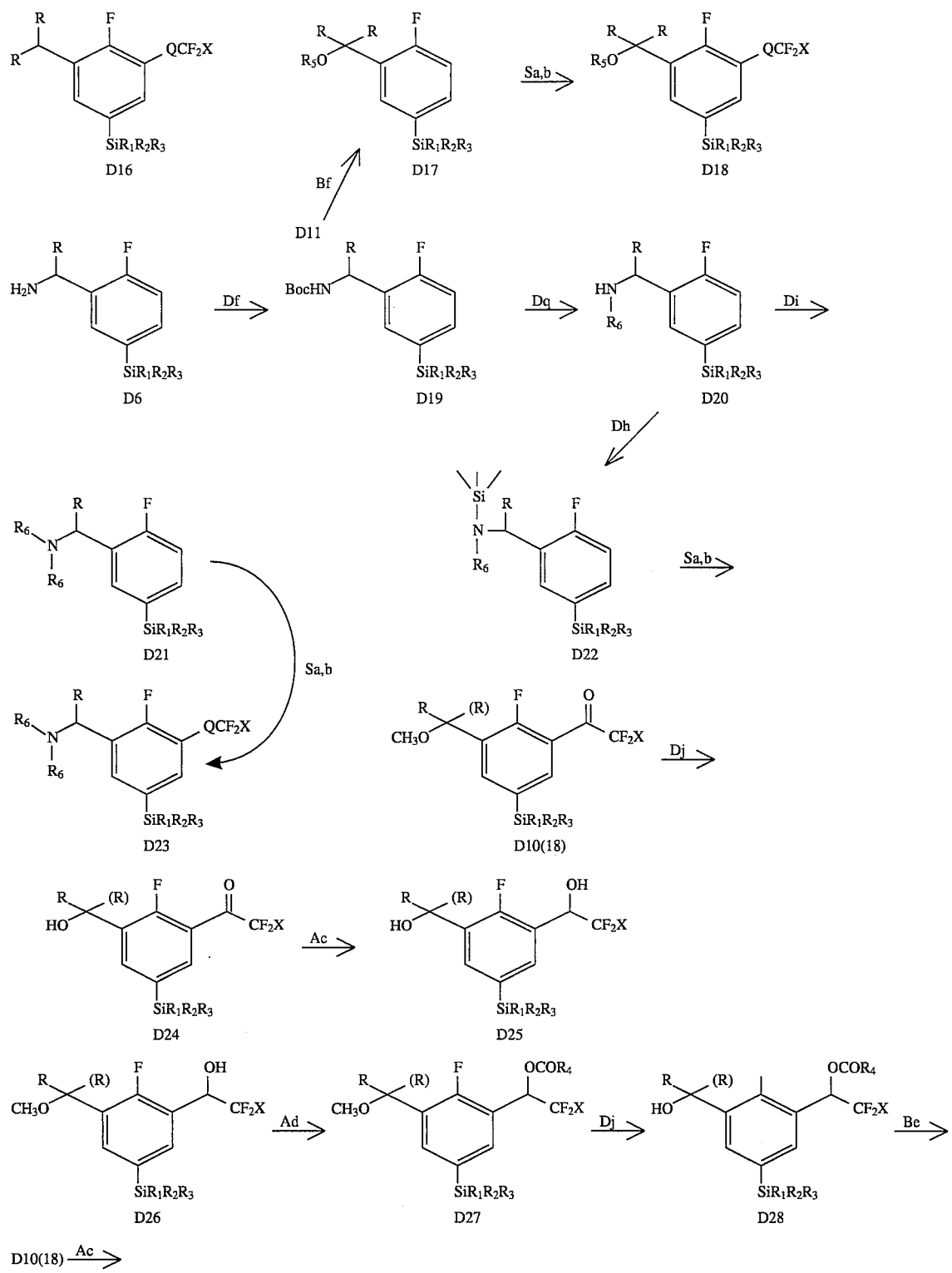
-continued
SCHEME D:

-continued
SCHEME D:

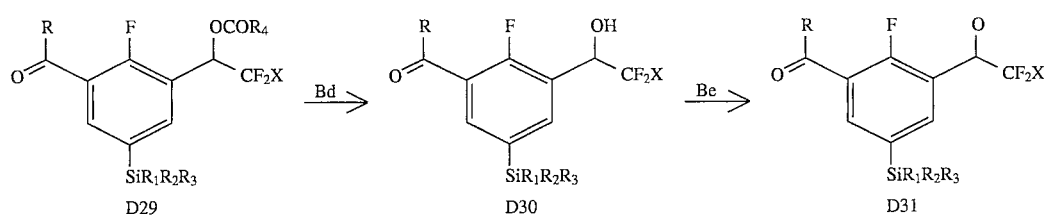

R is H or $(C_{1-10})$ alkyl

Step Da: $D_1=A_2 \rightarrow D_2$ or $D_{11}$:
Following the procedure described in Step Ab the lithium salts are treated with paraformaldehyde or aldehydes or ketones to produce benzyl alcohol derivatives $D_2$ or $D_{11}$.

Step Db: $D_2 \rightarrow D_3$ and $D_{11} \rightarrow D_{14}$
Benzyl alcohol derivatives $D_2$ or $D_{11}$ are treated with p-toluenesulfonylchloride in pyridine at 0° C. to produce tosyl derivatives $D_3$ or $D_{14}$.

Step Dc: $D_3 \rightarrow D_4$ and $D_{14} \rightarrow D_{15}$
Tosyl derivatives are reduced with lithium aluminum hydride in di-n-butyl ether to produce alkyl derivatives $D_4$ or $D_{15}$.

Step Dc':
Alternatively non-branched alkyl derivatives $D_4$ are produced by reaction of the lithium salt of $A_2$ (prepared as described in Step Ab) with a non-substituted alkyl bromide or iodide.

Step Dd: $D_2 \rightarrow D_6$
Benzyl alcohol derivatives $D_2$ are reacted with phthalimide in the presence of equimolar amounts of diethyl azodicarboxylate and triphenylphosphine in tetrahydrofuran to produce phtalimide derivatives which are then treated with hydrazine hydrate in ethanol or methanol to produce amine derivatives $D_6$.

Step De: $D_{11} \rightarrow D_{12}$
Benzyl alcohol derivatives $D_{11}$ are heated with trimethyl aluminum to produce alkyl derivatives $D_{12}$.

Step Df: $D_6 \rightarrow D_{19}$
Amine derivatives $D_6$ are reacted with di-tert-butyl dicarbonate with one equivalent of triethylamine in dichloromethane to produce N-Boc derivatives $D_{19}$.

Step Dg: $D_{19} \rightarrow D_{20}$
N-Boc derivatives $D_{19}$ are reacted with one equivalent of sodium hydride in tetrahydrofuran. The sodium salt intermediates are reacted with a bromo or iodo derivative of $R_6$ followed by hydrolysis with aqueous hydrochloric acid, Amine derivatives $D_{20}$ are purified as their free bases after neutralization of the aqueous phase.

Step Dh: $D_{20} \rightarrow D_{22}$
Following Step Bb amine derivatives $D_{20}$ are treated with one equivalent of alkyl lithium reagent followed by one equivalent of chlorotrimethylsilane to produce N-trimethylsilylamine derivatives $D_{22}$.

Step Di: $D_{20} \rightarrow D_{21}$
Following Step Dg amine derivatives $D_{20}$ are treated with one equivalent of sodium hydride and one equivalent of bromo or iodo derivative of $R_6$ followed by hydrolysis with water to produce amine derivatives $D_{21}$.

Step Dj: $D_{10}(D_{18}) \rightarrow D_{24}$ and $D_{27} \rightarrow D_{28}$
Methylbenzyl ether derivatives $D_9(D_{17})$ or $D_{27}$ are treated with boron tribromide or trimethylsilyliodide in dichloromethane to produce benzyl alcohols derivatives $D_{24}$ or $D_{28}$.

Other steps not specifically described are defined in the scheme as using steps previously described.

SCHEME E1: to make the subgeneric Formula VI:

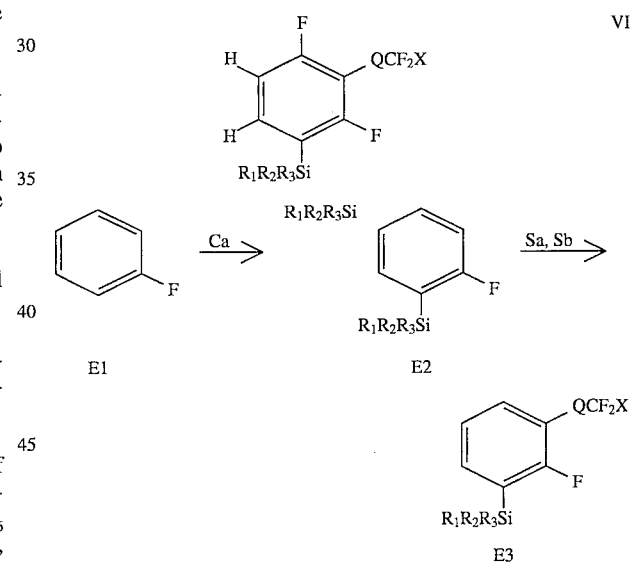

Step Ca: The same reaction is used as previously described in Scheme C, but with the starting materials shown in this scheme.

Steps Sa, Sb: Using the starting material shown in Scheme E1, the reaction is as described in Scheme A.

SCHEME E2: to make the subgeneric Formula VII:

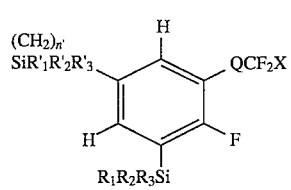

VII

-continued
SCHEME E2: to make the subgeneric Formula VII:
n = 1 or 2
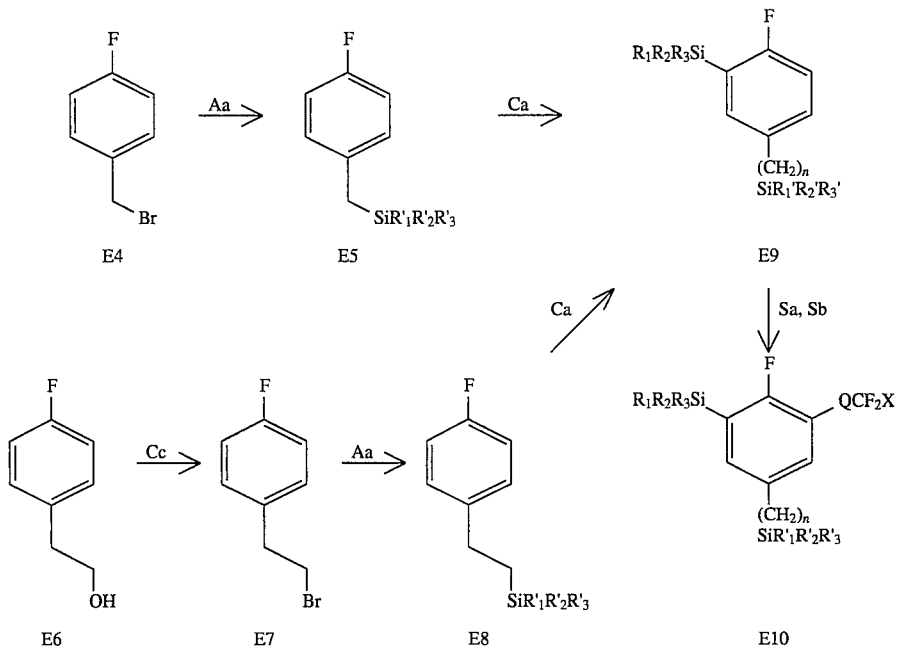
All reactions are as previously defined herein using the compounds shown above.
SCHEME E3: to make the subgeneric Formula VIII:
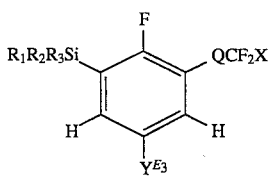
VIII
$Y^{E3}$ = $C_{1-6}$ Alkyl, $COR_4$, Hydroxyalkyl, Aminoalkyl, Alkoxyalkyl, N-Alkyl, or N,N-Dialkylaminoalkyl
Ts = tosyl or tosyl derivatives,
R = $C_{1-6}$ Alkyl.
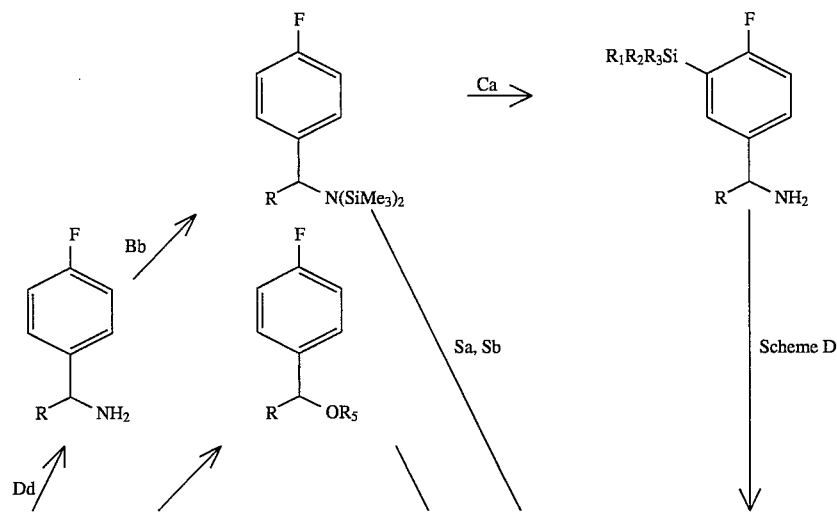

SCHEME E3: to make the subgeneric Formula VIII:

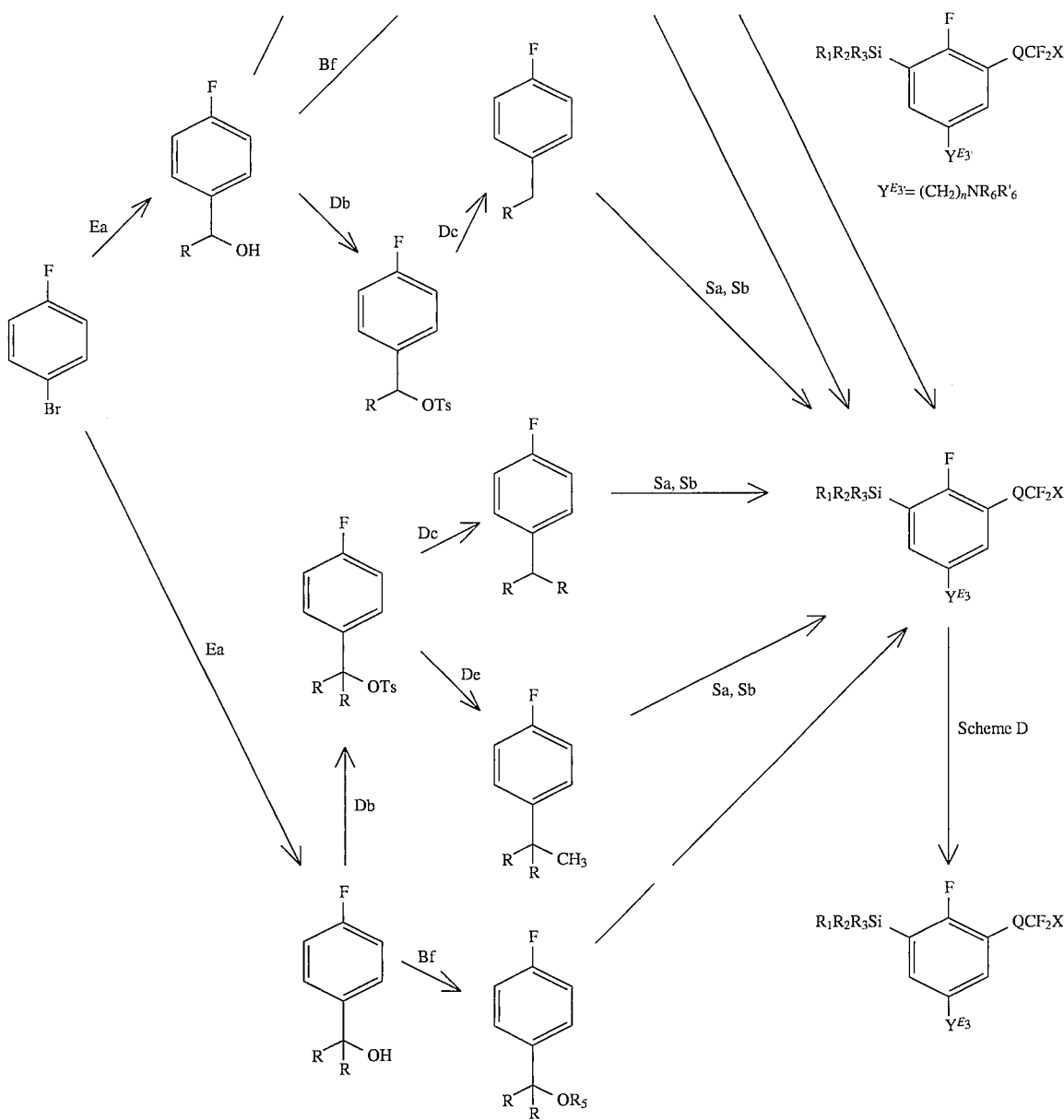

R = H or ($C_{1-10}$) alkyl,
TS = Tosyl or tosyl derivatives
n = 0, 1, or 2
$Y^{E3} = R_4(CO)$, hydroxy ($C_{1-6}$) alkyl, $(CH_2)_nR_6R'_6$ Step Ea: 4-Fluoro-1-bromobenzene is reacted with one equivalent of magnesium in diethyl ether or tetrahydrofuran. To this Grignard intermediate is added paraformaldehyde or aldehyde or ketone to produce benzyl alcohol derivatives.

SCHEME H: to make the subgeneric Formula IX:

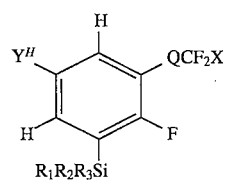

-continued
SCHEME H: to make the subgeneric Formula IX:

wherein
$Y^H$ = OH, $NH_2$, $NR_6R'_6$, $NO_2$, $N_3$, CN, $SO_3H$, $CO_2R_4$, Br, Cl, F, or $OR_5$;

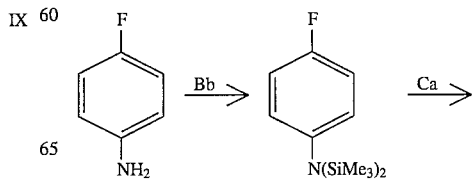

SCHEME H: to make the subgeneric Formula IX:

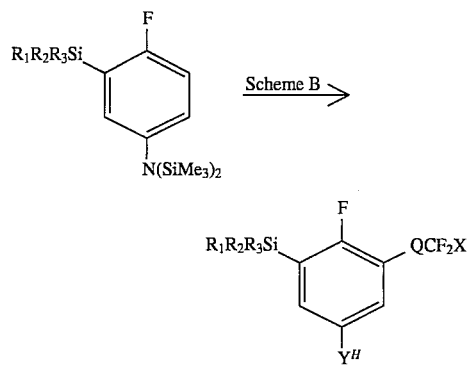

SCHEME J: to make the subgeneric Formula X:

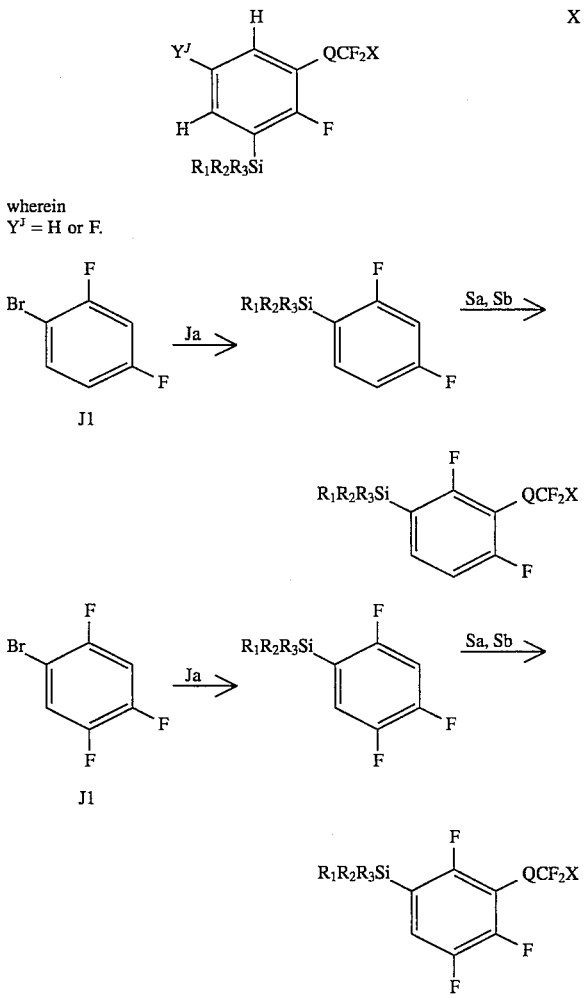

wherein
$Y^J$ = H or F.

Step Ja: 2,4-Difluoro-1-bromobenzene or 2,4,5-trifluoro-1-bromobenzene is treated with one equivalent of an alkyllithium reagent in diethyl ether or tetrahydrofuran at −78° C. The lithium salt intermediate is reacted with a chlorotrisubstituted silane at −50° C. to produce the corresponding silylated derivatives.

Steps Sa, Sb: As previously described using the compounds shown in Scheme J.

EXAMPLE 1

2,2,2-Trifluoro-1-(3-Trimethylsilyl-6-fluoro)phenyl ethanone

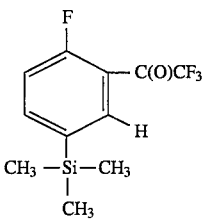

STEP A:
4-TRIMETHYLSILYL-1-FLUOROBENZENE

A solution of 17.5 g (100 mmol) of 4-bromo-1-fluorobenzene and 10.86 g (100 mmol) of chlorotrimethylsilane in 100 ml of tetrahydrofuran is added dropwise in 1.5 hour on 2.43 g (1.00 mg-atoms) of magnesium in 50 ml of tetrahydrofuran at reflux. Then the reaction mixture is refluxed 18 hours, cooled to 0° C. and hydrolized by the addition of 100 ml of 3N HCl. The organic layer is separated, washed with brine, dried over $MgSO_4$ and concentrated. 4-trimethyl-1-fluorobenzene is distilled to yield 13.45 g (80%); b.p. 64°–65° C./15 mmHg.

STEP B:
2,2,2-TRIFLUORO-1-(3-TRIMETHYLSILYL-6-FLUORO)PHENYL ETHANONE

To a solution of 8.40 g (50 mmol) of 4-trimethylsilyl-1-fluorobenzene in 50 ml of tetrahydrofuran at −50° C. is added dropwise 33.33 ml (50 mmol) of 1.5M n-butyl lithium in hexane. The reaction mixture is stirred 2 hours and then cooled to −78° C. A solution of 14.20 g (100 mmol) of ethyl trifluoroacetate in 40 ml of tetrahydrofuran is added dropwise and the reaction mixture is stirred 1 hour at −78° C. The cooling bath is removed and when the temperature rose to 0° C., 100 ml of 3N HCl is added. The organic layer is separated, washed with brine, dried over $MgSO_4$ and concentrated. Chromatography on silica gel (2% of ethyl acetate in petroleum ether) followed by distillation afforded 1.87 g (14%) of title compound; b.p. 120° C./14 mmHg.

EXAMPLE 2

2,2,2-Trifluoro-1-(3-trimethylsilyl-6-fluoro)phenyl ethanol

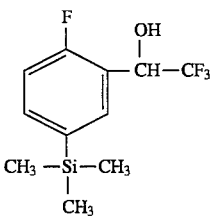

To a solution of 0.67 g (2.55 mmol) of 2,2,2-trifluoro-1-(3-trimethyl-6-fluoro)phenyl ethanone in 5 ml of ethanol at 0° C. is added 0.97 g (2.55 mmol) of sodium borohydride. The reaction mixture is stirred 1 hour at room temperature, cooled to 0° C. and hydrolized with 1.64 g (30.65 mmol) of ammonium chloride in 30 ml of water. The crude product is extracted with diethyl ether (2×30 ml), the organic layer is washed twice with brine, dried over $MgSO_4$ and concentrated. Chromatography on silica gel (5% of ethyl acetate in petroleum ether) followed by distillation afforded 0.54 g (80%) of the title compound; b.p. 145° C./19 mmHg.

EXAMPLE 3

2,2,2-Trifluoro-1-(2-fluoro-5-dimethylethylsilyl)phenyl ethanone

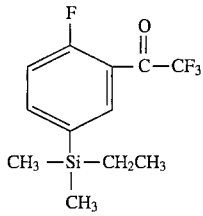

STEP A:
4-DIMETHYLETHYLSILYL-1-FLUOROBENZENE

Following the procedure described in Step A of the Example 1, title compound is obtained in 37% yield; b.p. 85°–87° C./17 mmHg.

STEP B:
2,2,2-TRIFLUORO-1-(2-FLUORO-5-DIMETHYLETHYLSILYL)PHENYL ETHANONE

Following the procedure described in Step B of the Example 1, title compound is obtained in 19% yield; b.p. 135° C./14 mmHg.

EXAMPLE 4

2,2,2-Trifluoro-1-(2-fluoro-3-trimethylsilyl)phenyl ethanone

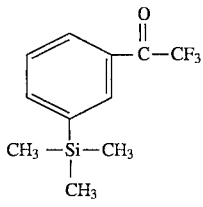

STEP A
2-TRIMETHYLSILYL-1-FLUOROBENZENE

To a solution of 4.8 g (50 mmol) of fluorobenzene in 50 ml of tetrahydrofuran at −50° C. is added dropwise 37.60 ml (50 mmol) of 1.33M n-butyl lithium hexane. The reaction mixture is stirred 6 hours while the temperature is kept between −40° C. and −50° C. To the solution is added 5.43 g (50 mmol) of chlorotrimethylsilane in 10 ml of tetrahydrofuran. The reaction mixture is stirred 3 hours at −50° C., 15 hours at room temperature and hydrolized with 5.35 g (100 mmol) of ammonium chloride in 50 ml of water. The organic layer is separated, washed with brine, dried over $MgSO_4$ and concentrated. Crude material is distilled in vacuo, yielding 0.37 g (3%); b.p. 42° C./15 mmHg.

STEP B:
2,2,2-TRIFLUORO-1-(2-FLUORO-3-TRIMETHYLSILYL)PHENYL ETHANONE

To a solution of 0.37 g (1.6 mmol) of 2-trimethylsilyl-1-fluorobenzene in 3.5 ml (1.6 mmol) is added 1.6M n-butyl lithium in hexane. The reaction mixture is stirred 6 hours at −50° C., cooled to −78° C. and a solution of 0.23 g (1.6 mmol) of ethyl trifluoroacetate in 2 ml of tetrahydrofuran is added. The reaction mixture, is stirred one hour at −78° C., 15 hours at room temperature and hydrolized with 5 ml of 1N HCl. The organic layer is separated, washed with brine, dried over $MgSO_4$ and concentrated. Chromatographon silica gel (5% of ethyl acetate in petroleum ether) afforded 0.12 g (28%) of the title compound.

EXAMPLE 5

2,2,2-Trifluoro-1-(2,6-difluro-3-trimethylsilyl)phenyl ethanone

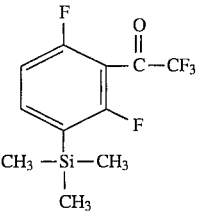

STEP A:
2,4-DIFLUORO-1-TRIMETHYLSILYLBENZENE

To a solution of 5.8 g (30 mmol) of 2,4-difluoro-1-bromobenzene in 40 ml of tetrahydrofuran at −78° C. is added dropwise 20 ml (30 mmol) of 1.5M n-butyl lithium in hexane. The reaction mixture is stirred 10 minutes at −78° C. Then a solution of 3.26 g (30 mmol) of chlorotrimethylsilane in 15 ml of tetrahydrofuran is added dropwise and the reaction mixture is stirred 7 hours between −60° C. and −50° C. To the reaction mixture is added 4.8 g (90 mmol) of ammonium chloride in 30 ml of water and the organic layer is separated, washed with brine, dried over $MgSO_4$ and concentrated. Title compound is purified by distillation.

STEP B:
2,2,2-TRIFLUORO-1-(2,6-DIFLUORO-3-TRIMETHYLSILYL)PHENYL ETHANONE

Title compound is prepared as described in step B of the Example 4 and purified by distillation.

EXAMPLE 6

2,2,2-Trifluoro-1-(2-fluoro-3-methoxymethyl-5-trimethylsilyl)phenyl ethanone

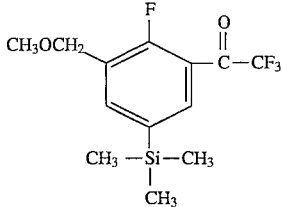

STEP A:
2-HYDROXYMETHYL-5-TRIMETHYLSILYL-1-FLUOROBENZENE

To a solution of 3.36 g (20 mmol) of 4-fluoro-1-trimethylsiyl benzene in 20 ml of tetrahydrofuran at −50° C. is added dropwise 13.33 ml (20 mmol) of 1.5M n-butyl lithium in hexane. The reaction mixture is stirred 6 hours while the temperature was kept between −50° C. and −60° C. To the solution was added 1.20 g (40 mmol) of paraformaldehyde by portion at −78° C. The reaction mixture is stirred one hour at −78° C., 15 hours at room temperature and hydrolized with 20 ml of 3N HCl. The organic layer is separated, washed with brine, dried over $MgSO_4$ and concentrated. The title compound is purified by distillation.

STEP B:
2-METOXYMETHYL-5-TRIMETHYLSILYL-1-FLUOROBENZENE

A solution of 1.98 g (10 mmol) of 2-hydroxymethyl-5-trimethylsilyl-1-fluorobenzene in 10 ml of tetrahydrofuran is added dropwise on a mixture of 0.24 g (10 mmol) of sodium hydride in 10 ml of tetrahydrofuran at 0° C. The reaction mixture is stirred 3 hours at room temperature and cooled to 0° C. A solution of 1.42 g (10 mmol) of iodomethane in 10 ml of tetrahydrofuran is added dropwise and the reaction mixture is stirred 15 hours at room temperature. A solution of 1.60 g (30 mmol) of ammonium chloride in 10 ml of water is added, the organic layer is separated, washed with brine, dried over MgSO₄ and concentrated. The title compound is purified by distillation.
STEP C:
2,2,2-TRIFLUORO-1-(2-FLUORO-3-METHOXYMETHYL-5-TRIMETHYLSILYL)PHENYL ETHANONE Title compound is prepared as described in step B of Example 4.

EXAMPLE 7

2,2,2-Trifluoro-1-(2-fluoro-3-hydroxymethyl-5-trimethylsilyl)phenyl ethanone

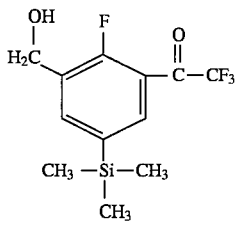

To a solution of 1.54 g (5 mmol) of 2,2,2-trifluoro-1-(2-fluoro-3-methoxymethyl-5-trimethylsilyl)phenyl ethanone in 10 ml of dichloromethane at −78° C. is added dropwise 5 ml (5 mmol) if 1M boron tribromide in dichloromethane. Cooling bath is removed and the reaction mixture is stirred one hour at room temperature. Then 2 ml of methanol is added dropwise, followed by 10 ml of water. The organic layer is separated, washed with brine, dried over MgSO₄ and concentrated. Title compound is recrystallized from isopropanol.

EXAMPLE 8

2,2,2-Trifluoro-1-(2-fluoro-3-n-butyl-5-trimethylsilyl)phenyl ethanone

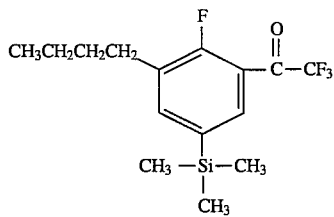

STEP A:
2-n-BUTYL-4-TRIMETHYLSILYL-1-FLUOROBENZENE

To a solution of 3.36 g (20 mmol) of 4-fluoro-1-trimethylsilylbenzene in 20 ml of tetrahydrofuran at −50° C. is added dropwise 13.33 ml (20 mmol) of 1.5M n-butyl lithium in hexane. The reaction mixture is stirred 4 hours between −40° C. and −50° C. and then 3.68 g (20 mmol) of n-iodobutane in 10 ml of tetrahydrofuran is added dropwise. The reaction mixture is stirred 4 hours between −40° C. and −50° C., cooling bath is removed and 20 ml of 1N HCl is added dropwise. The organic layer is separated, washed with brine, dried over MgSO₄ and concentrated. The title compound is purified by distillation.

STEP B:
2,2,2-TRIFLUORO-1-(2-FLUORO-3-n-BUTYL-5-TRIMETHYLSILYL)PHENYL ETHANONE

Title compound is prepared as described in step B of Example 4.

EXAMPLE 9

2,2,2-Trifluoro-1-(2-fluoro-3-amino-5-trimethylsilyl)phenyl ethanone hydrochloride

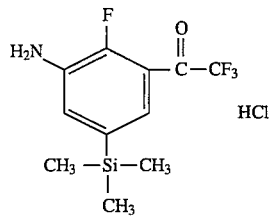

STEP A:
2-FLUORO-5-TRIMETHYLSILYL-BENZOIC ACID

To a solution of 8.4 g (50 mmol) of 4-fluoro-1-trimethylsilyl benzene in 50 ml of tetrahydrofuran at −60° C. is added dropwise 31.25 ml (50 mmol) of 1.6M n-butyl lithium in hexane and the reaction mixture is stirred 6 hours between −50° C. and −60° C. Then the reaction mixture is treated with excess of carbon dioxide, cooling bath is removed and 50 ml of water is added dropwise. Tetrahydrofuran is removed under reduced pressure and the aqueous solution is extracted twice with 30 ml of n-hexane. The aqueous layer is acidified with 20 ml of 6N HCl, extracted twice with 50 ml of ethyl acetate. The organic layers are combined, washed with brine, dried over MgSO₄ and concentrated. Title compound is recrystallized from isopropanol.
STEP B:
2-FLUORO-5-TRIMETHYLSILYL-ANILINE A mixture of 2.12 g (10 mmol) of 2-fluoro-5-trimethylsilyl-benzoic acid and 1.78 g (15 mmol) of thionyl chloride is heated 2 hours at 60° C. Then gases and excess of thionyl chloride are removed under reduced pressure. To the crude material dissolved in 10 ml of acetone is added dropwise 6.5 g (10 mmol) of sodium azide in 10 ml of water and the mixture is stirred one hour at 0° C. Acetone is removed under reduced pressure and the acyl azide was extracted with ethyl acetate. The organic phase is dried over MgSO₄ and ethyl acetate is removed under reduced pressure. To the acyl azide 20 ml of benzene is added and the reaction mixture is stirred 30 minutes at reflux. Then the solution is cooled to 0° C., 10 ml of concentrated hydrochloric acid is added and the mixture is heated 30 minutes at reflux. Benzene and water are removed under reduced pressure and the hydrochloride salt is recrystallized from isopropanol. To the salt dissolved in 10 ml of water is added 10 ml of 1N sodium hydroxide and the aqueous mixture is extracted with ethyl acetate. The organic layer is washed with brine, dried over MgSO₄ and concentrated to obtain pure 2-fluoro-5-trimethylsilyl-aniline.
STEP C:
2-FLUORO-5-TRIMETHYLSILYL-N,N-(bis-TRIMETHYLSILYL)ANILINE To a solution of 0.91 g (5 mmol) of 2-fluoro-5-trimethylsilyl-aniline in 10 ml of tetrahydrofuran at 0° C. is added dropwise 6.67 ml (10 mmol) of 1.5M n-butyl lithium in hexane and 10 minutes later 1.08 g (10 mmol) of chlorotrimethylsilane in 10 ml of tetrahydrofuran. Cooling bath is removed and the mixture is stirred one hour at reflux.

Solvents are removed under reduced pressure and title compound is purified by distillation.
STEP D:
2,2,2-TRIFLUORO-1-(2-FLUORO-3-AMINO-5-TRIMETHYLSILYL)PHENYL ETHANONE HYDROCHLORIDE TO a solution of 0.98 g (3 mmol) of 2-fluoro-5-trimethylsilyl-N,N-(bis-trimethylsilyl)aniline in 6 ml of tetrahydrofuran at −60° C. is added dropwise 2 ml (3 mmol) of 1.5M n-butyl lithium in hexane. The reaction mixture is stirred 6 hours between −50° C. and −60° C., cooled to −78° C. and a solution of 0.85 g (6 mmol) of ethyl trifluoroacetate in 6 ml of tetrahydrofuran is added dropwise. The reaction mixture is stirred one hour at −78° C., 15 hours at room temperature and hydrolized with 10 ml of 3N HCl. Organic solvents are removed under reduced pressure. The aqueous layer is extracted twice with diethyl ether, basified with 10 ml of 6N sodium hydroxide, extracted twice with ethyl acetate. The ethyl acetate layers are combined, washed with brine, dried over $MgSO_4$ and concentrated. Crude material is dissolved in diethyl ether and treated with a saturated solution of HCl in diethyl ether. The hydrochloride salt is filtered and recrystallized from isopropanol.

It is now established that Alzheimer's disease and other senile degenerative diseases such as senile dementia are characterized by a selective loss in the cerebral cortex of choline acetyltransferase, the enzyme responsible for the biosynthesis of acetylcholine. There also exists a good correlation between memory impairment or dementia and the decrement in cholinergic transmission. Thus, impaired cholinergic transmission in the central nervous system may be, at least in part, responsible for the symptomatology of Alzheimer's disease and senile dementia. In support to these conclusions such compounds as physostigmine and 1,2,3,4-tetrahydro-9-aminoacridine (THA), compounds which prevent the catabolism of acetylcholine have found a place in the treatment of Alzheimer's and other senile degenerative diseases. Indeed, it has been recognized that the extent of improvement of cognitive functions has been closely related to the degree of inhibition of acetylcholinesterase.

The compounds of the present invention are useful in treating other conditions responsive to inhibition of acetylcholinesterase such as Myasthenia Gravis [*J. Neurol. Neurosurg. Psychiatry,* 46 (10) 1983, 929–935, *Neurology* 42 (6) 1992, 1153–1156], antidotes against poisoning with organophosphates [see U.S. Pat. No. 5,171,750, *Int. J. Pharmacol. Ther. Toxicol.* 27 (8) 1989, 367–387], and glaucoma (*Arch. Clin. Exp. Ophthalmol.* 229 (3), 1991, 252–253).

The compounds of Formula I are pharmacologically active agents capable of inhibiting acetylcholinesterase as demonstrable in standard biological in vitro and in vivo test procedures. Indeed, based upon standard laboratory procedures, it is to be shown that the compounds of Formula I are potent and selective, quasi irreversible inhibitors of acetylcholinesterase capable of demonstrating advantages over the prior art,, particularly physostigmine, in their use in the treatment of Alzheimer's disease and senile dementia. The compounds, in general, will exert their acetylcholinesterase inhibitory properties within the dose range of about 0.01 mg to 5 mg per kilogram of body weight for the preferred compounds.

For pharmacological end-use applications, the compounds of Formula I are preferentially administered in the form of their pharmaceutically acceptable acid addition salts. Of course, the effective dosage of the compounds will vary according to the individual potency of each compound employed, the severity and nature of the disease being treated and the particular subject being treated. In general, effective results can be achieved by administering a compound at a dosage of about 0.01 mg to about 20 mg per kilogram of body weight per day, administered systemically. Therapy should be initiated at lower dosages. The dosage thereafter may be administered orally in solid dosage forms, e.g., capsules, tablets, or powders, or in liquid forms, e.g., solutions or suspensions. The compounds may also be injected parenterally in the form of sterile solutions or suspensions.

In practicing the method of this invention, the active ingredient is preferably incorporated in a composition comprising a pharmaceutical carrier and from about 5 to about 90 percent by weight of a compound of the invention or a pharmaceutically-acceptable salt thereof. The term "pharmaceutical carrier" refers to known pharmaceutical excipients useful in formulating pharmaceutically active compounds for internal administration to animals, and which are substantially non-toxic and non-sensitizing under conditions of use. The compositions can be prepared by known techniques for the preparation of tablets, capsules, elixirs, syrups, emulsions, dispersions and wettable and effervescent powders, and can contain suitable excipients known to be useful in the preparation of the particular type of composition desired.

The preferred route of administration is oral administration. For oral administration the formula I compounds can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptable surfactant, suspending agent, or emulsifying agent.

The formula I compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4methanol, ethers such as polyethylene glycol 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically acceptable adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl beta-aminopropionates, and 2-alkylimidazoline quarternary ammonium salts, as well as mixtures. The parenteral compositions of this invention will typically contain from about 0.5 to about 25% by weight of the formula I compound in solution. Preservatives and buffers may also be used advantageously. In order to minimize or eliminate irritation at the site of injection, such compositions may contain a non-ionic surfactant having a hydrophile-lipophile balance (HLB) of from about 12 to about 17 . The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951, 3,797,494, 3,996,934,and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

As is true for most classes of compounds suitable for use as therapeutic agents, certain subgeneric groups and certain specific compounds are preferred. Preferably, $R_1$, $R_2$, and $R_3$ are each methyl or ethyl, or mixtures thereof. Y is preferably hydrogen, —$(CH_2)_nOR_5$ wherein $R_5$ is $C_{1-10}$ alkyl, and more preferably, methyl, hydroxy ($C_{1-6}$ alkyl and more preferably alpha hydroxy $C_{1-6}$ alkyl, $C_{1-4}$ alkyl, or —$(CH_2)_NNR_6R_6'$ wherein N preferably is zero. Preferably, Z is F. Q is preferably C(O) or CH(OH). Y is preferably F. Z' is preferably H.

Specifically preferred compounds besides the compounds specifically exemplified are those charted below as follows:

| $R_1$ | $R_2$ | $R_3$ | Z' | Z | X | Y |
|---|---|---|---|---|---|---|
| Methyl | Methyl | Methyl | H | F | F | Methyl |
| Methyl | Methyl | Methyl | F | H | F | Methyl |
| Methyl | Methyl | Methyl | H | F | F | Isopropyl |
| Methyl | Methyl | Methyl | F | H | F | Isopropyl |
| Methyl | Methyl | Ethyl | F | H | F | H |
| Methyl | Methyl | Ethyl | H | F | F | Methyl |
| Methyl | Methyl | Ethyl | F | H | F | Methyl |
| Methyl | Methyl | Ethyl | H | F | F | Isopropyl |
| Methyl | Methyl | Ethyl | F | H | F | Isopropyl |
| Methyl | Ethyl | Ethyl | H | F | F | H |
| Methyl | Ethyl | Ethyl | F | H | F | H |
| Methyl | Ethyl | Ethyl | H | F | F | Methyl |
| Methyl | Ethyl | Ethyl | F | H | F | Methyl |
| Methyl | Ethyl | Ethyl | H | F | F | Isopropyl |
| Methyl | Ethyl | Ethyl | F | H | F | Isopropyl |
| Methyl | Methyl | Propyl | H | F | F | H |
| Methyl | Methyl | Propyl | F | H | F | H |
| Methyl | Methyl | Propyl | H | F | F | Methyl |
| Methyl | Methyl | Propyl | F | H | F | Methyl |
| Methyl | Methyl | Propyl | H | F | F | Isopropyl |
| Methyl | Methyl | Propyl | F | H | F | Isopropyl |

What is claimed is:

1. A compound of the formula:

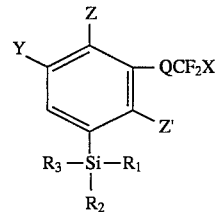

stereoisomers or mixtures thereof, or pharmaceutically acceptable salts thereof, wherein:

each of Z and Z' are independently H or F, provided that at least one of Z or Z' is F;

Q is

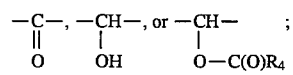

X is H, Br, Cl, F or $CF_3$;

Y is H, OH, ($C_{1-6}$) alkyl, —$(CH_2)_mOR_5$, hydroxy($C_{1-6}$)alkyl, —$(CH_2)_nNR_6R_6'$, azido, CN, $CO_2R_4$, $COR_6$, $SO_3H$, Br, Cl, F, $NO_2$ or —$(CH_2)_n$ $SIR_1'R_2'R_3'$, provided that when both Z and Z' are F, then Y is H or F;

$R_1$, $R_2$, $R_3$, $R_1'$, $R_2'$ and $R_3'$ are each independently $C_{1-10}$ alkyl or $(CH_2)_{n''}$aryl;

$R_4$ is H, $C_{1-10}$ alkyl, phenyl, benzyl or phenethyl;

$R_5$ is H, $C_{1-10}$ alkyl, benzyl or phenethyl;

$R_6$ and $R_6'$ are hydrogen or $C_{1-10}$ alkyl;

m is an integer of 0, 1, 2, 3 or 4; and n, n' and n" are each independently an integer of 0, 1 or 2.

2. The compound of claim 1 wherein each of $R_1$, $R_2$, $R_3$, $R_1'$, $R_2'$ and $R_3'$, when present are independently methyl.

3. The compound of claim 1 wherein Z is F.

4. The compound of claim 1 wherein Z' is H.

5. The compound of claim 1 wherein Q is C(O) or CH(OH).

6. The compound of claim 1 wherein the compound is 2,2,2-Trifluoro-1-(3-trimethylsilyl-6-fluoro)phenyl ethanone.

7. The compound of claim 1 wherein the compound 2,2,2-Trifluoro-1-(3-trimethylsilyl-6-fluoro)phenyl ethanol.

8. The compound of claim 1 wherein the compound is 2,2,2-Trifluoro-1-(2-fluoro-5-dimethylethylsilyl)phenyl ethanone.

9. The compound of claim 1 wherein the compound 2,2,2-Trifluoro-1-(2-fluoro-3-trimethylsilyl)phenyl ethanone.

10. The compound of claim 1 wherein the compound is 2,2,2-Trifluoro-1-(2,6-difluoro-3-trimethylsilyl)phenyl ethanone.

11. The compound of claim 1 wherein the compound is 2,2,2-trifluoro-1-(2-fluoro-3-methoxymethyl-5-trimethylsilyl)phenyl ethanone.

12. The compound of claim 1 wherein the compound is 2,2,2-trifluoro-1-(2-fluoro-3-hydroxymethyl-5-trimethylsilyl)phenyl ethanone.

13. The compound of claim 1 wherein the compound is 2,2,2-trifluoro-1-(2-fluoro-3-n-butyl-5-trimethylsilyl)phenyl ethanone.

14. The compound of claim 1 wherein the compound is 2,2,2-trifluoro-1-(2-fluoro-3-amino-5-trimethylsilyl)phenyl ethanone hydrochloride.

15. The process of making a compound of the formula:

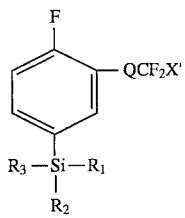   I stereoisomers or mixtures thereof, and pharmaceutically acceptable salts thereof, wherein:

Q is

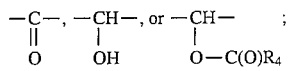

X' is H, Br, Cl, or F:

$R_1$, $R_2$, and $R_3$ are each independently $C_{1-10}$ alkyl or $(CH_2)_{n''}$aryl;

$R_4$ is H, $C_{1-10}$ alkyl, phenyl, benzyl or phenethyl;

m is an integer of 0, 1, 2, 3 or 4; and n" is an integer of 0, 1 or 2;

by converting the 4-fluorotrialkylsilylphenyl compound:

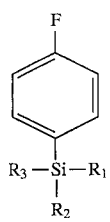

to the lithium salt, and the reactant is combined with the ester $XCF_2CO_2R$, with X being a halide and R being $C_{1-6}$ alkyl, or the acid lithium salt $XCF_2CO_2Li$ followed by hydrolysis to produce the ketone, wherein X' is H, Br, Cl or F:

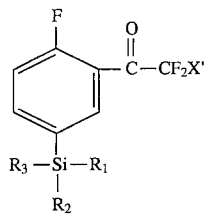

and the ketone may be hydrolyzed to the alcohol which may be subsequently esterified with an acyl chloride $ClCOR_4$.

16. A composition comprising the compound of claim 1 and a pharmaceutically acceptable carrier.

17. A method of treating a patient for degenerative dementias by administering to the patient an effective amount of the compound of claim 1.

* * * * *

UNITED STATES PATENT AND TRADEMARK OFFICE
CERTIFICATE OF CORRECTION

PATENT NO. : 5,523,442

DATED : Jun. 4., 1996

INVENTOR(s) : Collard et al.

It is certified that error appears in the above-identified patent and that said Letters Patent is hereby corrected as shown below:

Column 1, Lines 5 and 6 the patent reads: "PCT/US96/0672", and the number should be corrected to read -- PCT/US94/00720--

Column 6, Line 36 the patent reads: "[(ClCOR$_4$)]", and should read --(ClCOR$_4$)--.

Column 15, D13 the patent reads: "

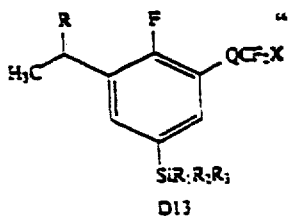

and should read --

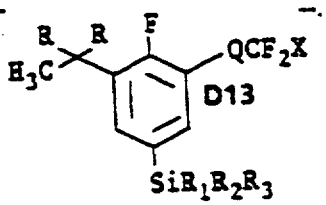

--.

UNITED STATES PATENT AND TRADEMARK OFFICE
CERTIFICATE OF CORRECTION

PATENT NO. : 5,523,442

DATED : Jun. 4, 1996

INVENTOR(s) : Collard et al.

It is certified that error appears in the above-identified patent and that said Letters Patent is hereby corrected as shown below:

Column 20, Line 23 the patent reads: "alcohols derivatives", and should read --alcohol derivatives--.

Column 20, Line 30 the patent reads: " 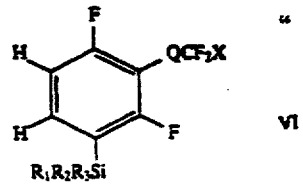 "

and should read -- 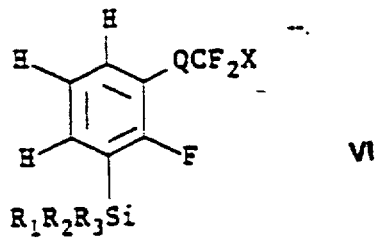 --.

Column 25, Line 50 the patent reads: "J1", and should read --J2--.

UNITED STATES PATENT AND TRADEMARK OFFICE
CERTIFICATE OF CORRECTION

PATENT NO. : 5,523,442

DATED : Jun. 4, 1996

INVENTOR(s) : Collard et al.

It is certified that error appears in the above-identified patent and that said Letters Patent is hereby corrected as shown below:

Column 27, Line 35 the patent reads: " 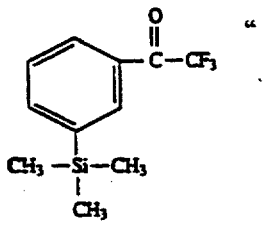 "

and should read -- 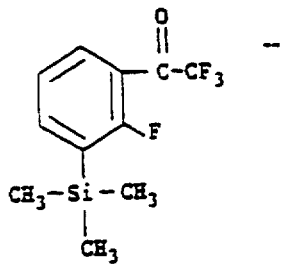 --

Column 27, Line 65 the patent reads: "Chromatographon", and should read --Chromatograph on--.

Column 28, Line 1 the patent reads: "difluro", and should read --difluoro--.

UNITED STATES PATENT AND TRADEMARK OFFICE
CERTIFICATE OF CORRECTION

PATENT NO. : 5,523,442

DATED : Jun. 4, 1996

INVENTOR(s) : Collard et al.

It is certified that error appears in the above-identified patent and that said Letters Patent is hereby corrected as shown below:

Column 31, Line 7 the patent reads: "TO", and should read --To--.

Column 32, Line 65 the patent reads: "4methanol", and should read --4-methanol--.

Signed and Sealed this

Tenth Day of November 1998

*Attest:*

*Attesting Officer*

BRUCE LEHMAN

*Commissioner of Patents and Trademarks*